United States Patent
Gibbs et al.

(10) Patent No.: US 6,458,161 B1
(45) Date of Patent: Oct. 1, 2002

(54) METHOD AND APPARATUS FOR ACETABULAR RECONSTRUCTION

(75) Inventors: Phillip M. Gibbs, Winona Lake, IN (US); Allen D. Boyd, Jr., Rochester, NY (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/792,174

(22) Filed: Feb. 23, 2001

(51) Int. Cl.[7] ................................................. A61F 2/32
(52) U.S. Cl. ................................. 623/22.32; 623/22.38
(58) Field of Search .......................... 623/22.22, 22.23, 623/22.38, 22.32

(56) References Cited

U.S. PATENT DOCUMENTS

| | | | | |
|---|---|---|---|---|
| 3,840,904 A | * | 10/1974 | Tronzo | 623/23.32 |
| 4,743,262 A | * | 5/1988 | Tronzo | 623/22.32 |
| 5,176,711 A | * | 1/1993 | Grimes | 623/23.32 |
| 5,211,665 A | * | 5/1993 | Ku | 623/22.32 |
| 5,314,490 A | | 5/1994 | Wagner et al. | |
| 5,326,367 A | | 7/1994 | Robioneck | |
| 5,326,368 A | | 7/1994 | Collazo | |
| 5,370,704 A | * | 12/1994 | Decarlo | 623/22.32 |
| 5,702,477 A | | 12/1997 | Capello et al. | |
| 5,871,548 A | | 2/1999 | Sanders et al. | |
| 5,931,870 A | | 8/1999 | Cuckler et al. | |
| 6,162,257 A | | 12/2000 | Gustilo et al. | |
| 6,273,891 B1 | * | 8/2001 | Masini | 623/22.32 |
| 6,306,173 B1 | * | 10/2001 | Masini | 623/22.32 |

OTHER PUBLICATIONS

Michael S. Bradfors, M.D. and Wayne G. paprosky, M.D., F.A.C.S., Total Acetabular Transplant Allograft Reconstruction of the Severely Deficient Acetabulum, Sunrise Hospital and Medical Center, Las Vegas, NV and Rush–Presbyterian–St. Lukes Medical Center, Chicago, IL, 1995 by W.B. Saunders Company, pp. 1–15.

Overview of Anatomy, Clinically Oriented Anatomy, pp. 1–16.

\* cited by examiner

*Primary Examiner*—Michael J. Milano
(74) *Attorney, Agent, or Firm*—Harness, Dickey & Pierce, P.L.C.

(57) ABSTRACT

An acetabular prosthesis for implantation in an acetabulum and surrounding pelvis is described. The acetabular prosthesis includes an acetabular cup having a substantially concave inner surface and a substantially convex outer surface, wherein an area defining a groove is located on the outer surface of the acetabular cup. An optional spacer member, having a raised ridge formed on a surface thereof, slidably engages the groove. The spacer provides augmentation and load bearing support in cases where bone tissue loss has occurred in and around the acetabulum. A fastener, such as a surgical screw, is used to secure the acetabular cup, and the optional spacer, to the acetabulum. At least one attachment member is integrally formed with the acetabular cup for fastening to a surface of the pelvis, such as the ilium and/or the ischium. Another optional spacer member is provided for the attachment member to provide augmentation around the attachment points on the pelvis. A fastener, such as a surgical screw, is used to secure the attachment member, and the other optional spacer, to the pelvis. The described acetabular prosthesis is especially useful in revision hip implant procedures where significant bone tissue loss has occurred either in or around the acetabulum and/or the pelvis.

57 Claims, 6 Drawing Sheets

METHOD AND APPARATUS FOR ACETABULAR RECONSTRUCTION

FIELD OF THE INVENTION

This invention relates generally to a method and apparatus for use in orthopedic surgery and, more particularly, to a method and apparatus for providing a modular acetabular prosthesis having various modular attachment components for use during an orthopedic surgical procedure.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is snugly fit and supported by the host femur. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis. One example of such a device is generally known as a protrusio cage.

In this regard, a revision acetabular prosthesis will generally include additional mounting points, such as integral extension members or hooks that provide additional stability for the revision acetabular prosthesis. These additional mounting points are generally required due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what is known as an ilium flange that is formed integral with the acetabular prosthesis and enables further securement of the acetabular prosthesis in the ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons' preferences. Moreover, the surgeon will generally have to have several revision acetabular cups available during surgery to account for any type of condition that may arise during the surgical procedure. This increased inventory of prosthetic devices increases the overall hospital costs and inventory control. Furthermore, by requiring the multiple revision acetabular cups to be available during the surgical procedure, multiple prosthetic devices must be sterilized prior to the surgical procedure, thereby increasing the surgical time, cost and complexity.

As previously noted, during hip revision procedures, surgeons often encounter significant defects due to osteolysis at the acetabular implant site or due to the removal of bone tissue that has become attached to the removed acetabular implant. These defects are usually filled with bulk bone allograft, bone cement, or morselized bone graft. Each material type raises it's own set of concerns.

With respect to bulk bone allograft, many doubts exist as to whether significant portions of a bulk allograft actually become viable over time. Dead allograft may not provide long term structural support. Additionally, higher infection rates are sometimes connected to the use of bulk allograft. Finally, bulk allograft is also expensive and sometimes unavailable or difficult to obtain.

With respect to bone cement, when defects are filled with bone cement, subsequent revision procedures may be made more difficult because there is even less bone tissue to work with.

With respect to morselized bone graft, this has become the material of choice; however, it may not provide significant structural support. Motion of the acetabular implant is of real concern. For example, motion can prevent bone tissue from infiltrating the porous surface of the acetabular implant and thus can place too much load on a thin walled acetabular implant and screws, potentially causing them to fail. Additionally, morselized bone graft is very expensive and is sometimes unavailable or difficult to obtain.

What is needed then is a method and apparatus for providing a modular acetabular prosthesis having various modular attachment components for use during an orthopedic surgical procedure. This will, in turn, provide more surgical flexibility during implantation of the acetabular prosthesis, provide the surgeon with a variety of surgical options at the time of the surgical procedure, provide a universal acetabular cup that can be configured for use in many circumstances, reduce hospital inventory and inventory tracking requirements, and reduce the overall surgical time, cost and complexity.

SUMMARY OF THE INVENTION

In accordance with a first embodiment of the present invention, an acetabular prosthesis for implantation in an acetabulum and surrounding pelvis is provided, the acetabular prosthesis comprising: (1) an acetabular cup having a substantially concave inner surface and a substantially convex outer surface, the outer surface operable to be received in the acetabulum; (2) an area defining a receptacle located in the outer surface of the acetabular cup; (3) a spacer member having an appendage formed on a surface thereof for mating engagement with the receptacle, wherein the spacer member is disposed between the outer surface of the acetabular cup and the acetabulum; and (4) an attachment member integral with the acetabular cup for fastening to a surface of the pelvis.

In accordance with a second embodiment of the present invention, an acetabular prosthesis for implantation in an acetabulum and surrounding pelvis is provided, the acetabular prosthesis comprising: (1) an acetabular cup having a substantially concave inner surface and a substantially convex outer surface, the outer surface operable to be received in the acetabulum; (2) an attachment member integral with the acetabular cup for fastening to a surface of the pelvis; and (3) a spacer member adjacent to the attachment member, wherein the spacer member is disposed between the attachment member and the surface of the pelvis.

In accordance with a third embodiment of the present invention, a method for implanting an acetabular prosthesis in an acetabulum and surrounding pelvis is provided, comprising: (1) providing an acetabular cup having a substantially concave inner surface and a substantially convex outer surface, the outer surface operable to be received in the acetabulum, the outer surface of the acetabulum cup having an area defining a receptacle located therein, the acetabular cup having an attachment member integral therewith for fastening to a surface of the pelvis; (2) providing a spacer member having an appendage formed on a surface thereof for mating engagement with the receptacle; (3) securing the spacer member to the outer surface of the acetabular cup; (4) engaging the outer surface of acetabular cup with the acetabulum such that the spacer member is disposed between the outer surface of the acetabular cup and the acetabulum; (5) securing the acetabular cup to the acetabulum; and (6) securing the attachment member to the surface of the pelvis.

In accordance with a fourth embodiment of the present invention, a method for implanting an acetabular prosthesis in an acetabulum and surrounding pelvis is provided, comprising: (1) providing an acetabular cup having a substantially concave inner surface and a substantially convex outer surface, the outer surface operable to be received in the acetabulum, the acetabular cup having an attachment member integral with the acetabular cup for fastening to a surface of the pelvis; (2) providing a spacer member adjacent to the attachment member; (3) securing the spacer member to the attachment member; (4) engaging the outer surface of acetabular cup with the acetabulum such that the spacer member is disposed between the attachment member and the surface of the pelvis; (5) securing the acetabular cup to the acetabulum; and (6) securing the spacer member and the attachment member to the surface of the pelvis.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

The following description of the preferred embodiments concerning a method and apparatus for providing a modular acetabular prosthesis for use in orthopedic surgical procedures are merely exemplary in nature and are not intended to limit the invention or its application or uses. Moreover, while the present invention is described in detail below with reference to performing a revision type implantation procedure, it will be appreciated by those skilled in the art that the present invention is clearly not limited to only revision type orthopedic surgical procedures and may be used with various other orthopedic surgical procedures as well.

Referring to FIGS. 1–5, an acetabular prosthesis 10, according to the general teachings of the present invention, is shown. The acetabular prosthesis 10 includes a modified hemispherical acetabular cup 12. The acetabular cup 12 is said to be "hemispherical" in that it is not a perfect hemisphere; but rather, it includes an arcuate portion 14 extending along the periphery thereof without extending beyond the hemisphere of the acetabular cup 12.

The acetabular cup 12 is preferably constructed from any suitable biocompatible material, such as titanium, stainless steel, titanium alloy, cobalt-chrome-molybdenum alloy, and the like.

It should be noted that the acetabular cup 12 would normally also be associated with other components, such as a congruent shell or bearing liner (not shown) retained within the acetabular cup 12, via bone cement or a ring lock (not shown), which are not depicted for purposes of clarity.

The acetabular cup 12 preferably includes a substantially concave inner surface 16 and a substantially convex outer surface 18, wherein the outer surface 18 is operable to be received in the acetabulum. The inner surface 16 is preferably smooth, whereas the outer surface 18 may be smooth or roughened with a porous surface layer (not shown) to facilitate bone tissue in-growth.

An area defining an optional receptacle or groove 20 is located in at least a portion of the outer surface 18 of the acetabular cup 12. The groove 20 preferably includes tapered end portions 22, 24. The groove 20 is preferably located in proximity to a peripheral surface of the acetabular cup 12, and generally in the superior region of the acetabular cup 12. The exact purpose of the groove 20 will be explained later in detail.

The acetabular cup 12 preferably includes at least one, and more preferably, a plurality of throughbores 26 located therein. It should be noted that the groove 20 is bisected by at least one of the throughbores 26. The throughbores 26 provide a number of functions, such as enabling fastening members (not shown) to pass through the acetabular cup 12. Additionally, the throughbores 26 provide for the infiltration of bone cement to improve adhesion, as well as providing for new bone tissue in-growth. At least one of the throughbores 28 includes a threaded surface 30 thereon for receiving an insertion instrument (not shown) for properly aligning the acetabular prosthesis 10 within the acetabulum. Throughbore 28 also includes a recessed area 28A which permits the insertion instrument (not shown) to securely engage the acetabular cup 12 and permits controlled rotation of same. It will be noted that any graft material and/or bone cement should preferably be placed into the acetabulum before securing the acetabular cup 12 thereto.

A more specific description of the typical installation of an acetabular prosthesis can be found in U.S. Pat. Nos. 5,314,490; 5,326,367; 5,326,368; 5,702,477; 5,871,548; 5,931,870; and 6,162,257, the entire specifications of which are incorporated herein by reference.

The acetabular cup 12 preferably includes at least one, and more preferably, three substantially rigid attachment or extension members 32, 34, and 36 integrally formed with the acetabular cup 12 for fastening the acetabular prosthesis 10 to at least a portion of one or more surfaces of the pelvis (not shown), such as the ilium and/or the ischium. Preferably, attachment member 32 is used for attachment to the ischium, whereas attachment members 34 and 36 are used for attachment to various surfaces of the ilium (e.g., anterior and posterior).

Attachment member 32 is shown as being substantially triangularly shaped; however, it is envisioned that the shape may be altered to other configurations. It will be noted that attachment member 32 has two distinct portions, i.e., a first substantially curved portion 32A originating from, and contiguous with, the inner surface 16 of the acetabular cup 12, and a second substantially planar portion 32B extending out from, and angling away from, the first portion 32A. The curvature profile may be modified to meet any anatomical requirements.

Attachment member 32 preferably includes at least one, and more preferably, a plurality of throughbores located therein. In this view, a throughbore 38 is provided in the curved portion 32A and another throughbore 40 is provided in the planar portion 32B. The throughbores 38, 40 provide a number of functions, such as enabling fastening members such as a surgical screw (not shown) to pass therethrough in order to allow the fastening member 32 to be secured to the ischium.

Attachment member 34 is shown as being substantially rectangularly shaped; however, it is envisioned that the shape may be altered to other configurations. It will be noted that attachment member 34 has two distinct portions, i.e., a first substantially curved portion 34A originating from, and contiguous with, the inner surface 16 of the acetabular cup 12, and a second substantially planar portion 34B extending out from, and angling away from, the first portion 34A. The curvature profile may be modified to meet any anatomical requirements.

Attachment member 34 preferably includes at least one, and more preferably, a plurality of throughbores 42 located therein. In this view, additional throughbores 42A and 42B are provided in the curved portion 34A. The throughbores 42, 42A, and 42B provide a number of functions, such as enabling fastening members such as a surgical screw (not shown) to pass therethrough in order to allow the fastening member 34 to be secured to at least a portion of a surface of the ilium.

Attachment member 36 is also shown as being substantially rectangularly shaped; however, it is envisioned that the shape may be altered to other configurations. It will be noted that attachment member 36 also has two distinct portions, i.e., a first substantially curved portion 36A originating from, and contiguous with, the inner surface 16 of the acetabular cup 12, and a second substantially planar portion 36B extending out from, and angling away from, the first portion 36A. Again, the curvature profile may be modified to meet any anatomical requirements.

Attachment member 36 preferably includes at least one, and more preferably, a plurality of throughbores 44 located therein. In this view, an additional throughbore 44A is provided in the curved portion 36A. The throughbores 44 and 44A provide a number of functions, such as enabling fastening members such as a surgical screw (not shown) to pass therethrough in order to allow the fastening member 36 to be secured to at least another portion of a surface of the ilium spaced away from attachment member 34.

The installation of the acetabular prosthesis 10 would be accomplished in any number of ways, as are currently known in the art. The surgeon would surgically prepare the acetabulum and surrounding pelvic area to receive the acetabular prosthesis 10. This preparation would typically include removing any debris (e.g., bone fragments, bone cement) from the acetabulum. The surgeon would then install an allograft, if necessary, and install bone cement, if necessary, into the acetabulum. The acetabular cup 12 would then be received into, and anatomically aligned with, the acetabulum. At least one fastening member, such as a surgical screw, would then be placed through one of the throughbores 26 and into the interior of acetabulum, thus securing the acetabular cup 12 to the acetabulum. The attachment members 32, 34, and 36 would then be secured to the ischium and ilium, respectively, with fastening members, such as surgical screws.

However, if the acetabulum and/or the surrounding pelvic structures have any significant defects present, the loading will be borne primarily by the allograft and/or bone cement material, as previously described. Therefore, it is desirable to have the surfaces of the acetabular prosthesis 10 actually abut against the respective surfaces of the acetabulum and/or the surrounding pelvic structures, as opposed to using allografts and bone cement to fill the gap therebetween. Because the acetabular prosthesis 10 is constructed of metallic material, it is much stronger than allografts and bone cement, and therefore is much more able to withstand the loads and forces associated with standing, walking, and running activities.

Therefore, the present invention preferably employs at least one augment or spacer member to compensate for the fact that the acetabulum and/or the surrounding pelvic structures may have defects therein which prevent the outer surface 18 of the acetabular cup 12 from contacting the surface of the acetabulum, and/or the outer surfaces 32C, 34C, and 36C, respectively, from contacting the respective surfaces of the pelvis, i.e., the ischium and the ilium.

The spacer members are preferably constructed from any suitable biocompatible material, such as titanium, stainless steel, titanium alloy, cobalt-chrome-molybdenum alloy, etc. and is preferably made of the titanium alloy Ti-6Al-4V.

Referring to FIGS. 6–9, several different types of acetabular spacer members 60, 62, and 64 for use with the outer surface 18 of the acetabular cup 12, according to the general teachings of the present invention, are shown. It should be noted that only one spacer member would generally be used at a time in practice; however, multiple spacer members may be used in some instances. For example, if there is a relatively small defect in the superior region of the acetabulum, acetabular spacer member 60 can be employed. If there is a larger defect, either acetabular spacer member 62 or 64 may be used. It is envisioned that either smaller and/or larger acetabular spacer members may also be employed with the present invention.

The acetabular spacer members 60, 62, and 64 are preferably substantially curved so that the lower surfaces 60A, 60B, and 60C, substantially conform to the curvature of the outer surface 18 of the acetabular cup 12. Additionally, the acetabular spacer members 60, 62, and 64 preferably include an area defining a substantially curved and raised appendage or ridge 66, 68, and 70 formed on the lower surface 60A, 60B, and 60C, respectively, thereof for mating, and more preferably, sliding engagement with the groove 20. Finally, each acetabular spacer member 60, 62, and 64 preferably has at least one throughbore 72. The throughbores 72 preferably include a threaded surface 74 thereon. It should be noted that the raised ridges 66, 68, and 70 are bisected by the respective throughbore 72.

The purpose of the raised ridges 66, 68, and 70, respectively, is to allow the respective acetabular spacer member 60, 62, or 64 to slidingly mate with the groove 20 on the outer surface 18 of the acetabular cup 12. This allows the surgeon the option of positioning the respective acetabular spacer member 60, 62, or 64 practically anywhere along the length of the groove 20 to best deal with the particular acetabular defect in the superior-posterior region. For example, the acetabular spacer member 60, 62, or 64 can slide in a superior-posterior direction with respect to the acetabulum. It is also envisioned that the acetabular spacer member 60, 62, or 64 can slide in a medial direction, as well. Once the final position of the acetabular spacer member is determined, the surgeon can then secure the respective acetabular spacer member to the acetabular cup 12 by inserting a fastening member, such as a surgical screw, through one or more available throughbores 72 which preferably aligns with one or more of the throughbores 26 which bisect the groove 20. The screw would preferably extend upwardly through the acetabular cup 12 and into the respective acetabular spacer member, with the screw tip not extending past the upper surface of the respective acetabular spacer member. The modified acetabular prosthesis 10 can then be installed in the acetabulum, as previously described, such that the acetabular spacer member 60, 62, or 64 is disposed between the outer surface 18 of the acetabular cup 12 and the acetabulum.

Unfortunately, the use of acetabular spacer members 60, 62, or 64 alone is sometimes not enough to address each and every particular clinical situation. The use of the acetabular spacer members 60, 62, or 64 may address the defect in the acetabulum, but it may not address a defect in the surrounding pelvic structures, or alternatively, the use of the acetabular spacer members 60, 62, or 64 may alter the attachment point of the attachment members 32, 34 or 36 such that an undesirable gap is created between the respective outer surfaces 32C, 34C, and 36C and the pelvis.

Therefore, the present invention employs at least one other augment or spacer member to compensate for the fact that the surrounding pelvic structures may have defects therein which prevent the outer surfaces 32C, 34C, and 36C of rigid attachment members 32, 34, and 36, respectively, from contacting the respective surfaces of the pelvis, i.e., the ischium and the ilium.

Figure 1:
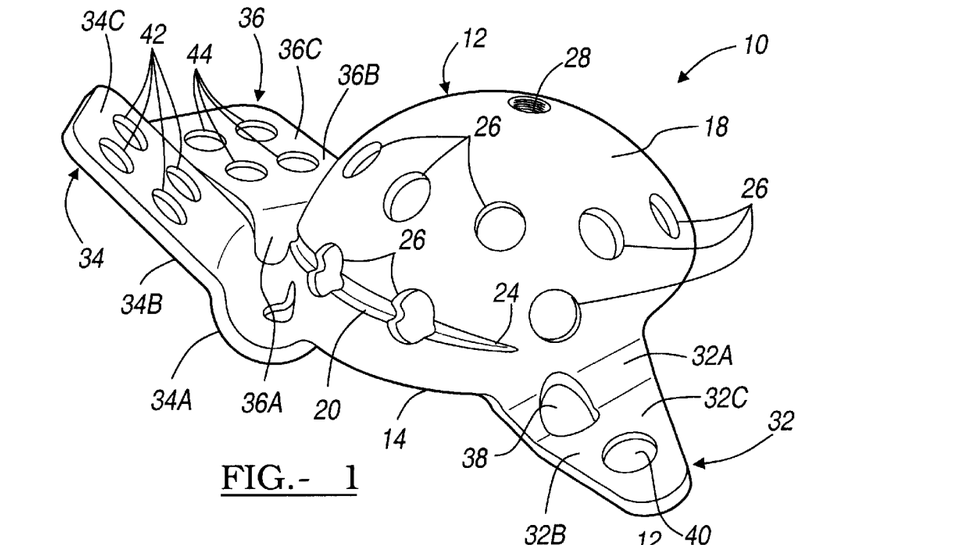
FIG. 1 is a rear perspective view of an acetabular prosthesis, in accordance with one embodiment of the present invention.
Figure 2:
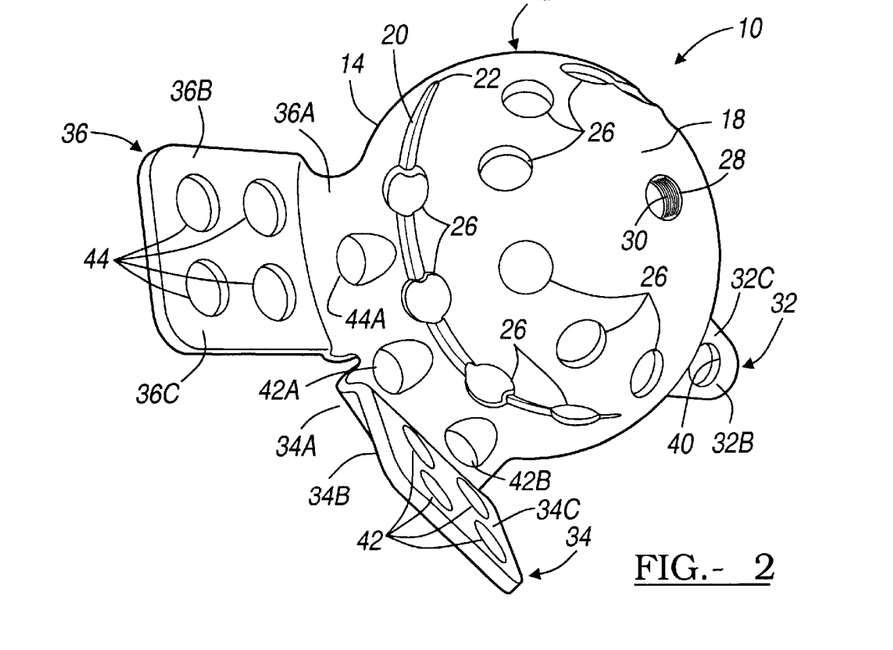
FIG. 2 is another rear perspective view of an acetabular prosthesis, in accordance with one embodiment of the present invention.
Figure 3:
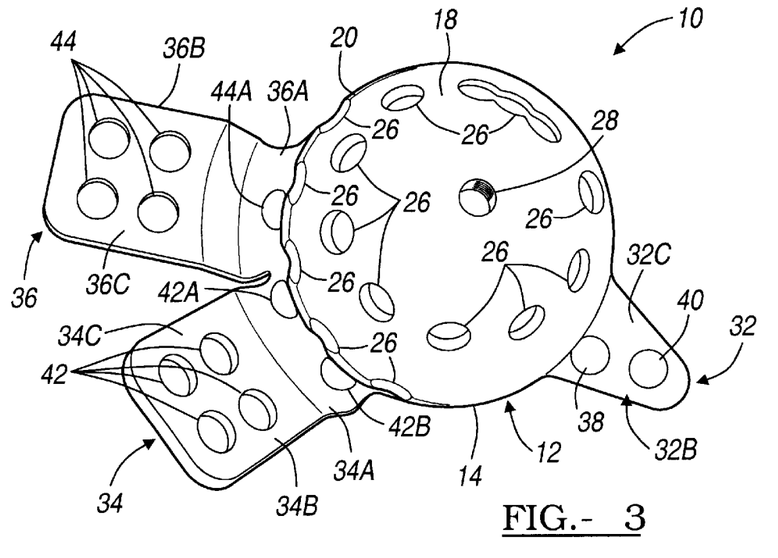
FIG. 3 is a rear elevational view of an acetabular prosthesis, in accordance with one embodiment of the present invention.
Figure 4:
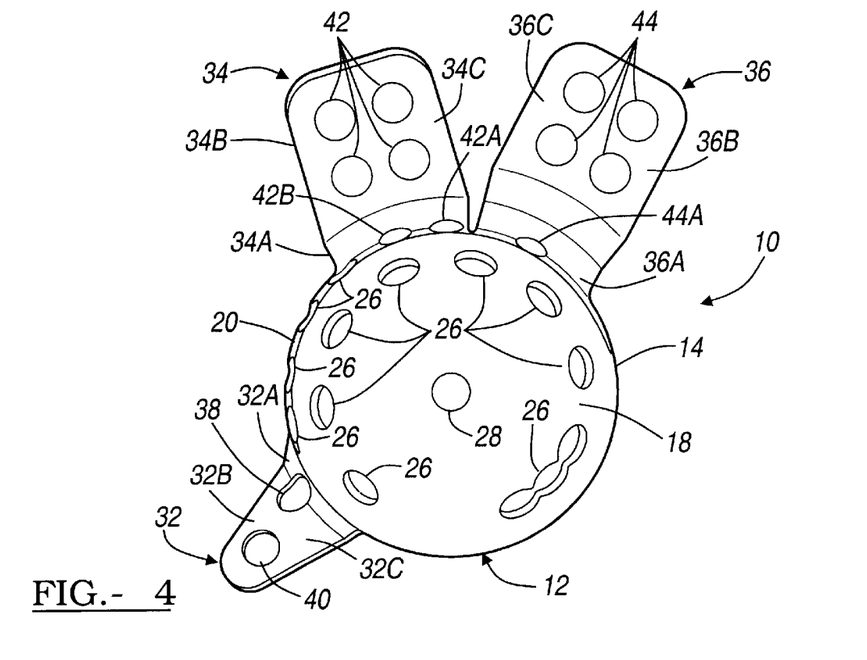
FIG. 4 is a rear plan view of an acetabular prosthesis, in accordance with one embodiment of the present invention.
Figure 5:
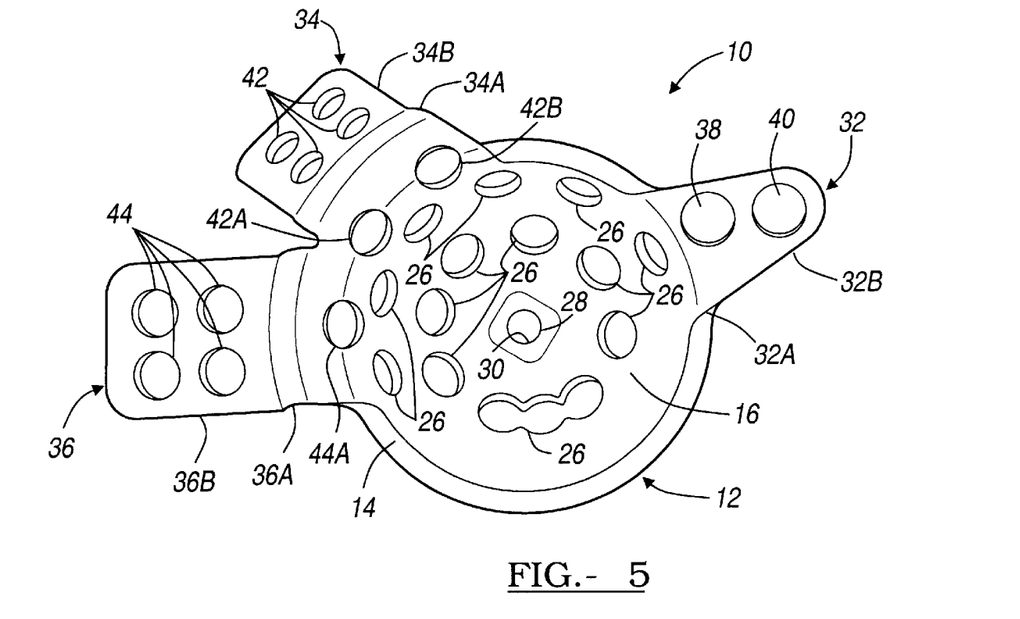
FIG. 5 is a front plan view of an acetabular prosthesis, in accordance with one embodiment of the present invention.
Figure 6:
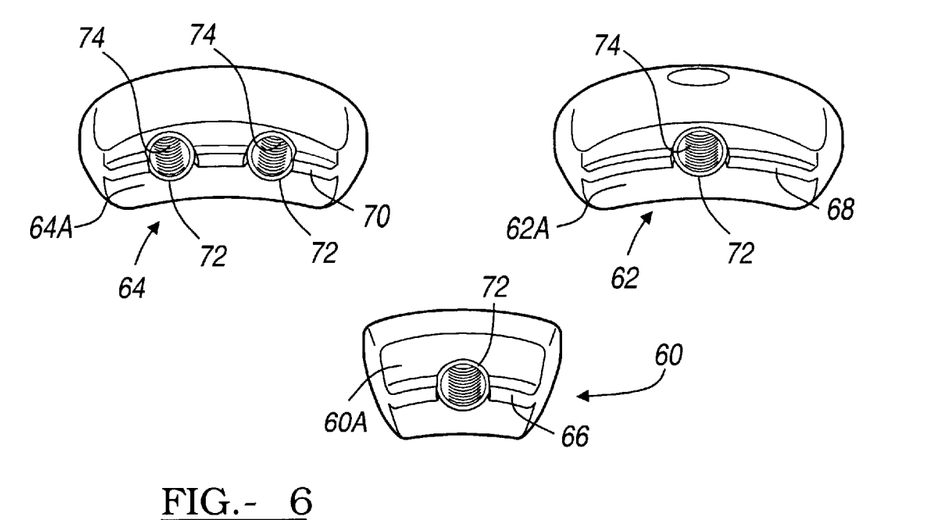
FIG. 6 is a side perspective view of several acetabular spacer members for an acetabular prosthesis, in accordance with one embodiment of the present invention.
Figure 7:
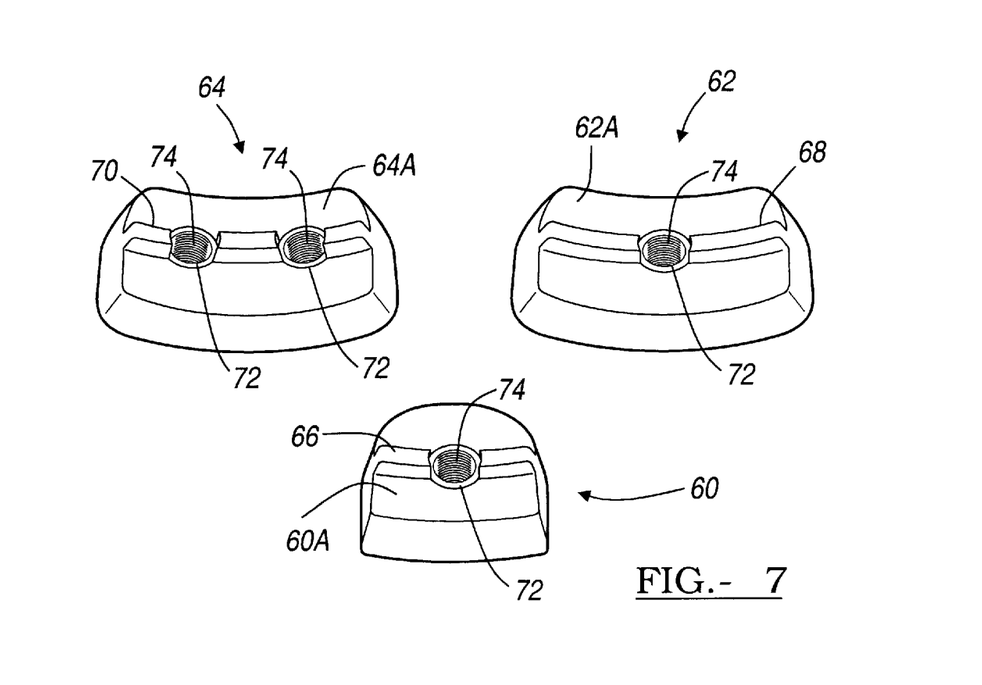
FIG. 7 is a bottom plan view of several acetabular spacer members for an acetabular prosthesis, in accordance with one embodiment of the present invention.
Figure 8:
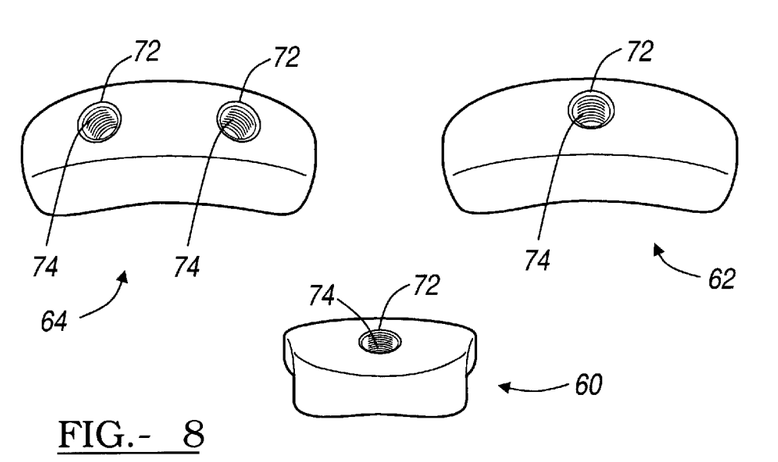
FIG. 8 is a top perspective view of several acetabular spacer members for an acetabular prosthesis, in accordance with one embodiment of the present invention.
Figure 9:
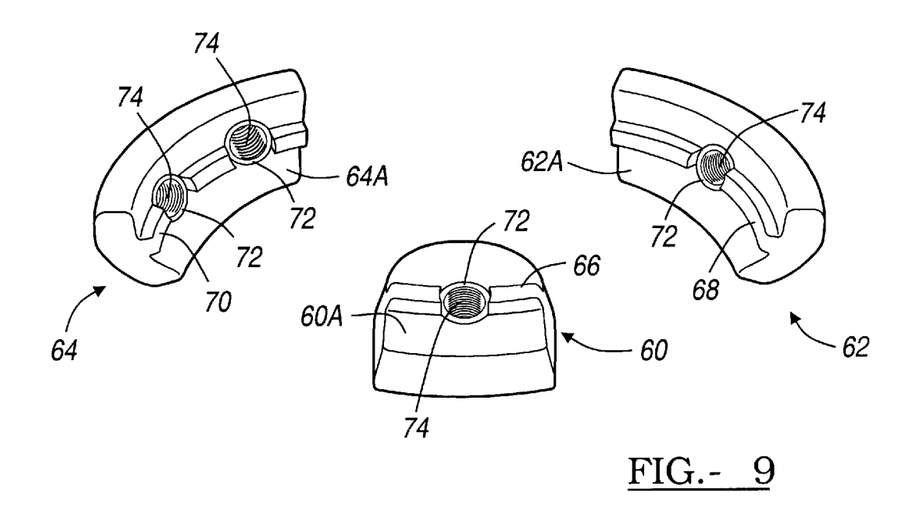
FIG. 9 is a bottom perspective view of several acetabular spacer members for an acetabular prosthesis, in accordance with one embodiment of the present invention.
Figure 10:
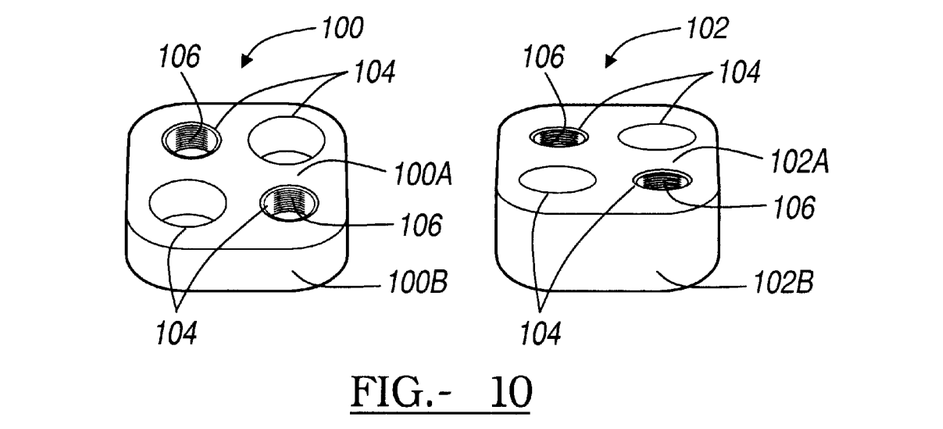
FIG. 10 is a front perspective view of two attachment spacer members for an acetabular prosthesis, in accordance with one embodiment of the present invention.
Figure 11:
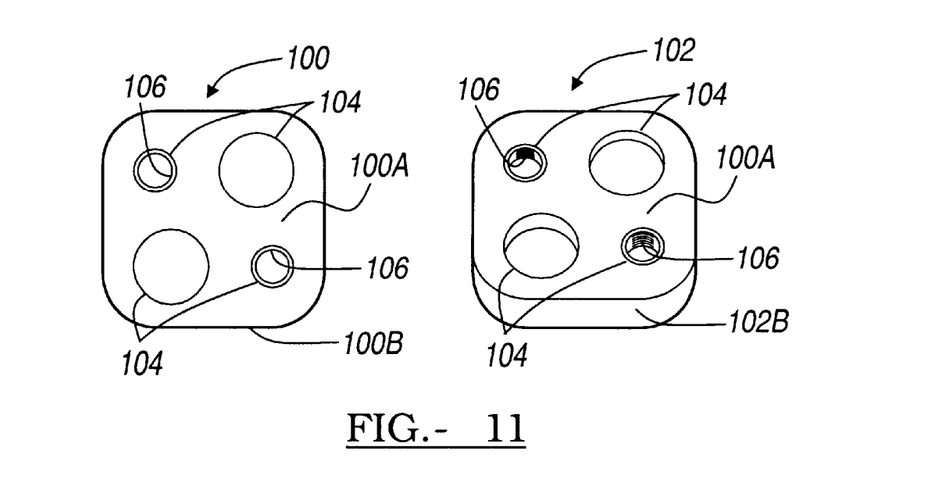
FIG. 11 is a top plan view of two attachment spacer members for an acetabular prosthesis, in accordance with one embodiment of the present invention.
Figure 12:
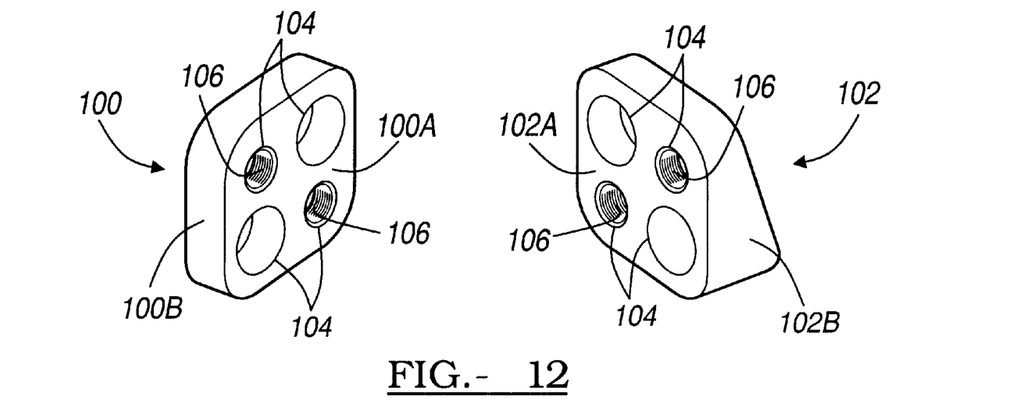
FIG. 12 is a side perspective view of two attachment spacer members for an acetabular prosthesis, in accordance with one embodiment of the present invention.

Referring to FIGS. 10–12, two different types of attachment spacer members 100 and 102 for use with the attachment members 32, 34, and 36, respectively, according to the general teachings of the present invention, are shown. It should be noted that more than one attachment spacer member can be used at one time in practice. For example, if there is a relatively small defect in the surface of the ischium, or attachment member 32 can not abut it, an attachment spacer member 100 or 102 can be employed. If there is a defect in the surface of the ilium (either anterior and/or posterior), or attachment member 34 or 36 can not abut it, an attachment spacer member 100 or 102 can be employed. It is envisioned that either smaller and/or larger attachment spacer members may also be employed with the present invention.

The attachment spacer members 100 and 102 preferably have at least one flat surface 100A and 102A, respectively, for mating adjacently against the planar portions 32B, 34B, and 36B of attachment members 32, 34, and 36, respectively. The other surface of the attachment spacer members 100 and 102 may be either flat and parallel 100B or flat and non-parallel (i.e., inclined) 102B.

Each attachment spacer member 100 and 102 preferably has at least one throughbore 104. At least one of the throughbores 104 preferably include a threaded surface 106 thereon. The surgeon can then secure the respective attachment spacer member 100 or 102 to the outer surface 32C, 34C, or 36C, respectively, by inserting a fastening member, such as a surgical screw, through one or more available throughbores 104 which preferably aligns with one or more of the throughbores 40, 42, 44, respectively, in planar portions 32B, 34B, or 36B, respectively. The further modified acetabular prosthesis 10 then can be installed in the acetabulum, as previously described, such that the attachment spacer members 100 and/or 102 are disposed between the outer surface 32C, 34C, or 36C, respectively, of the planar portions 32B, 34B, or 36B, respectively, of the attachment members 32, 34, or 36, respectively, and the pelvis, i.e., the ischium and/or the ilium. Preferably, two diagonally opposed and spaced throughbores 104 are used to attach the attachment spacer member 100 and 102 to the outer surface 32C, 34C, or 36C, respectively, of the planar portions 32B, 34B, or 36B, respectively, of the attachment members 32, 34, or 36, respectively, and the pelvis, i.e., the ischium and/or the ilium. Bone screws (not shown) can then be inserted through the two diagonally opposed throughbores 104, and the aligned one or more of the throughbores 40, 42, 44, respectively, to secure the attachment members 32, 34, or 36, respectively, to the pelvis.

It should be noted that sometimes it is only necessary to use the attachment spacer members 100 and/or 102 alone, instead of using them in conjunction with an acetabular spacer member 60, 62, or 64. In that scenario, it is beneficial that the groove 20 is employed in the outer surface 18 of the acetabular cup 12, as opposed to a raised appendage or ridge which may interfere with the proper alignment of the acetabular cup 12, or might irritate the acetabulum.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. An acetabular prosthesis for implantation in an acetabulum and surrounding pelvis, the acetabular prosthesis comprising:

an acetabular cup having a substantially concave inner surface and a substantially convex outer surface, the outer surface operable to be received in the acetabulum;

an area defining a receptacle located in the outer surface of the acetabular cup;

a spacer member having an appendage formed on a surface thereof for mating engagement with the receptacle;

wherein the spacer member is disposed between the outer surface of the acetabular cup and the acetabulum; and an attachment member integral with the acetabular cup for fastening to a surface of the pelvis.

2. The invention according to claim 1, wherein the receptacle comprises a groove.

3. The invention according to claim 1, wherein the appendage is slidably received in the receptacle.

4. The invention according to claim 1, wherein the appendage comprises a raised ridge.

5. The invention according to claim 1, wherein the acetabular cup include a throughbore.

6. The invention according to claim 5, wherein the throughbore includes a threaded surface.

7. The invention according to claim 5, wherein the receptacle is bisected by the throughbore.

8. The invention according to claim 1, wherein the receptacle is located in proximity to a peripheral surface of the acetabular cup.

9. The invention according to claim 1, wherein the acetabular cup has a substantially arcuate peripheral surface.

10. The invention according to claim 1, wherein the spacer member has a substantially curved surface.

11. The invention according to claim 1, wherein the appendage has a substantially curved surface.

12. The invention according to claim 1, wherein the spacer member has a throughbore.

13. The invention according to claim 12, wherein the appendage is bisected by the throughbore.

14. The invention according to claim 12, wherein the throughbore includes a threaded surface.

15. The invention according to claim 1, wherein the attachment member is contiguous with the inner surface of the acetabular cup.

16. The invention according to claim 1, wherein the attachment member has a throughbore.

17. The invention according to claim 1, wherein the attachment member is substantially planar.

18. The invention according to claim 1, wherein the attachment member extends outwardly away from the acetabular cup.

19. The invention according to claim 1, wherein the attachment member has a first portion and a second portion, wherein the second portion is angled with respect to the first portion.

20. The invention according to claim 1, wherein the surface of the pelvis is selected from the group consisting of the ilium, the ischium, and combinations thereof.

21. The invention according to claim 1, further comprising a second spacer member.

22. The invention according to claim 21, wherein the second spacer member is adjacent to the attachment member.

23. The invention according to claim 21, wherein the second spacer member includes a throughbore.

24. The invention according to claim 23, wherein the throughbore includes a threaded surface.

25. The invention according to claim 21, wherein the second spacer member includes a first surface and a second opposed and spaced surface.

26. The invention according to claim 25, wherein the first surface is substantially parallel to the second surface.

27. The invention according to claim 25, wherein the first surface is substantially non-parallel to the second surface.

28. The invention according to claim 1, further comprising a second attachment member.

29. The invention according to claim 28, further comprising a third attachment member.

30. An acetabular prosthesis for implantation in an acetabulum and surrounding pelvis, the acetabular prosthesis comprising:

an acetabular cup having a substantially concave inner surface and a substantially convex outer surface, the outer surface operable to be received in the acetabulum;

an attachment member integral with the acetabular cup for fastening to a surface of the pelvis; and a spacer member adjacent to the attachment member;

wherein the spacer member is disposed between the attachment member and the surface of the pelvis.

31. The invention according to claim 30, wherein the acetabular cup includes an area defining a groove located in the outer surface therein.

32. The invention according to claim 31, further comprising a second spacer member having an area defining a raised ridge formed on a surface thereof for sliding engagement with the groove, wherein the second spacer member is disposed between the outer surface of the acetabular cup and the acetabulum.

33. The invention according to claim 30, wherein the acetabular cup includes a throughbore.

34. The invention according to claim 33, wherein the throughbore includes a threaded surface.

35. The invention according to claim 33, wherein the groove is bisected by the throughbore.

36. The invention according to claim 31, wherein the groove is located in proximity to a peripheral surface of the acetabular cup.

37. The invention according to claim 30, wherein the acetabular cup has a substantially arcuate peripheral surface.

38. The invention according to claim 32, wherein the second spacer member has a substantially curved surface.

39. The invention according to claim 32, wherein the raised ridge has a substantially curved surface.

40. The invention according to claim 32, wherein the second spacer member has a throughbore.

41. The invention according to claim 40, wherein the raised ridge is bisected by the throughbore.

42. The invention according to claim 40, wherein the throughbore includes a threaded surface.

43. The invention according to claim 30, wherein the attachment member is contiguous with the inner surface of the acetabular cup.

44. The invention according to claim 30, wherein the attachment member has at least one throughbore.

45. The invention according to claim 30, wherein the attachment member is substantially planar.

46. The invention according to claim 30, wherein the attachment member extends outwardly away from the acetabular cup.

47. The invention according to claim 30, wherein the attachment member has a first portion and a second portion, wherein the second portion is angled with respect to the first portion.

48. The invention according to claim 30, wherein the surface of the pelvis is selected from the group consisting of the ilium, the ischium, and combinations thereof.

49. The invention according to claim 30, wherein the spacer member includes at least one throughbore.

50. The invention according to claim 49, wherein the throughbore includes a threaded surface.

51. The invention according to claim 30, wherein the spacer member includes a first surface and a second opposed and spaced surface.

52. The invention according to claim 51, wherein the first surface is substantially parallel to the second surface.

53. The invention according to claim 51, wherein the first surface is substantially non-parallel to the second surface.

54. The invention according to claim 30, further comprising a second attachment member.

55. The invention according to claim 54, further comprising a third attachment member.

56. A method for implanting an acetabular prosthesis in an acetabulum and surrounding pelvis, comprising:

providing an acetabular cup having a substantially concave inner surface and a substantially convex outer surface, the outer surface operable to be received in the acetabulum, the outer surface of the acetabulum cup having an area defining a receptacle located therein, the acetabular cup having an attachment member integral therewith for fastening to a surface of the pelvis;

providing a spacer member having an appendage formed on a surface thereof for mating engagement with the receptacle;

securing the spacer member to the outer surface of the acetabular cup;

engaging the outer surface of acetabular cup with the acetabulum such that the spacer member is disposed between the outer surface of the acetabular cup and the acetabulum;

securing the acetabular cup to the acetabulum; and securing the attachment member to the surface of the pelvis.

57. A method for implanting an acetabular prosthesis in an acetabulum and surrounding pelvis, comprising:

providing an acetabular cup having a substantially concave inner surface and a substantially convex outer surface, the outer surface operable to be received in the acetabulum, the acetabular cup having an attachment member integral with the acetabular cup for fastening to a surface of the pelvis;

providing a spacer member adjacent to the attachment member;

securing the spacer member to the attachment member;

engaging the outer surface of acetabular cup with the acetabulum such that the spacer member is disposed between the attachment member and the surface of the pelvis;

securing the acetabular cup to the acetabulum; and securing the spacer member and the attachment member to the surface of the pelvis.

* * * * *